United States Patent [19]
Paul et al.

[11] Patent Number: 5,697,958
[45] Date of Patent: Dec. 16, 1997

[54] ELECTROMAGNETIC NOISE DETECTOR FOR IMPLANTABLE MEDICAL DEVICES

[75] Inventors: Patrick J. Paul; David Prutchi, both of Lake Jackson, Tex.

[73] Assignee: Intermedics, Inc., Angleton, Tex.

[21] Appl. No.: 475,489

[22] Filed: Jun. 7, 1995

[51] Int. Cl.$^6$ .................................................... A61N 1/16
[52] U.S. Cl. ............................ 607/31; 607/32; 607/60; 128/901
[58] Field of Search .................................. 128/901, 903; 607/31, 32, 60, 9, 2

[56] References Cited

U.S. PATENT DOCUMENTS

| | | | |
|---|---|---|---|
| 3,218,638 | 11/1965 | Honig | 607/60 |
| 3,631,860 | 1/1972 | Lopin . | |
| 4,091,818 | 5/1978 | Brownlee et al. . | |
| 4,102,345 | 7/1978 | Cannon, III . | |
| 4,126,139 | 11/1978 | Walters et al. . | |
| 4,263,919 | 4/1981 | Levin | 128/901 |
| 4,424,812 | 1/1984 | Lesnick . | |
| 4,830,006 | 5/1989 | Haluska et al. . | |
| 4,967,746 | 11/1990 | Vandegriff . | |
| 5,010,887 | 4/1991 | Thornander | 128/901 |
| 5,020,538 | 6/1991 | Morgan et al. | 128/901 |
| 5,151,832 | 9/1992 | Pritchard et al. | 128/901 |
| 5,304,206 | 4/1994 | Baker, Jr. et al. . | |
| 5,350,413 | 9/1994 | Miller . | |
| 5,383,912 | 1/1995 | Cox et al. . | |
| 5,438,990 | 8/1995 | Wahlstrand et al. . | |

FOREIGN PATENT DOCUMENTS

| | | |
|---|---|---|
| 0713714A2 | 5/1996 | European Pat. Off. . |
| 9105912 U | 5/1991 | Germany . |

OTHER PUBLICATIONS

"Surface Mount Zero Bias Schottky Detector Diodes Technical Data" technical information publication of Hewlett-Packard Co., Sep., 1994, 12 pages.

"Cardiac Pacing and Electrophysiology", 3rd edition, edited by El-Sherif, N. and Samet, P., pp. 608–633, Barold, S.S., Falkoff, M.D., Ong, L.S. and Heinle, R.A. Interference in Cardiac Pacemakers: Exogenous Sources, W.B. Saunders Company, 1991.

Brown, J. "GMR Materials: Theory and Applications" Sensors, Sep., 1994, pp. 42–44, 47 and 48.

Carey, J. "Magnetic Field of Dreams" Business Week, Apr. 18, 1994, 3 pages starting at p. 118.

Denny, H.W. and Jenkins, B.M. "EMC History of Cardiac Pacemakers" EMC Test & Design, Apr., 1993, pp. 33, 35 and 36.

Lucas, E.H., Johnson, D. and McElroy, B.P. "The Effects of Electronic Article Surveillance Systems on Permanent Cardiac Pacemakers: An In Vitro Study" PACE, vol. 17, Nov., 1994, Part II, pp. 2021–2026.

Dodinot, B., Godenir, J-P., Costa, A.B., Zeller, C. and Broschart, M. "Electronic Article Surveillance: A Possible Danger for Pacemaker Patients" PACE, vol. 16, Jan., 1993, Part I, pp. 46–53.

(List continued on next page.)

Primary Examiner—Marvin M. Lateef
Assistant Examiner—Kennedy J. Schaetzle
Attorney, Agent, or Firm—E. Richard Zamecki

[57] ABSTRACT

Disclosed are apparatus and method for detecting electromagnetic interference (EMI), or noise, that may disrupt the proper operation of medical devices implantable in patients, such as cardiac stimulators. Circuitry of the detector of the invention is independent of other circuitry of the medical device. EMI is magnetically induced on an antenna that may be within the metal housing of the device in a receiver circuit, and the EMI signals are output to the noise detector. A variety of alert signals may be provided to the medical device circuitry to warn of the presence of EMI so that appropriate responses may be taken to insure the safety of the patient dependent on the device. The detector may share the telemetry antenna of the medical device, or utilize a separate, dedicated antenna to receive EMI. Alternative antennas external to the metal housing of the medical device include leads from the device to the heart of the patient, and a dedicated antenna in the non-metal header of the device.

29 Claims, 5 Drawing Sheets

OTHER PUBLICATIONS

Schuder, J.C., Gold, J.H. and Stephenson, H.E., Jr. "An Inductively Coupled RF System for the Transmission of 1 kW of Power Through the Skin" IEEE Transactions on Bio–Medical Engineering, vol. BME–18, No. 4, Jul., 1971, pp. 265–273.

Heetderks, W.J. "RF Powering of Millimeter–and Submillimeter–Sized Neural Prosthetic Implants" IEEE Transactions on Bio–Medical Engineering, vol. 35, No. 5, May, 1988, pp. 323–327.

Donaldson, P.E.K. "Power for Neurological Prostheses: A Simple Inductive R.F. Link with Improved Performance" J. Biomed. Eng., vol. 9, Jul., 1987, pp. 194–197.

"GMR Magnetic Bridge Sensor" technical information material of Nonvolatile Electronics, Inc., 2 pages.

"Rapid Prototype Integrated GMR Magnetic Sensors" technical information material of Nonvolatile Electronics, Inc., 2 pages.

"Integrated GMR Magnetic Sensors" technical information material of Nonvolatile Electronics, Inc., 2 pages.

Ivall, T. "Does Your Coupling Coefficient Matter?" Electronics & Wireless World, Jun., 1987, pp. 577–579.

ELECTROMAGNETIC NOISE DETECTOR FOR IMPLANTABLE MEDICAL DEVICES

TECHNICAL FIELD

The present invention relates to techniques for detecting electromagnetic fields which may cause interference to implantable medical devices, and particularly to methods and apparatus for identifying electromagnetic noise so that appropriate responses can be effected by the implantable devices to avoid malfunction thereof caused by the noise. The present invention finds particular application to implantable neuromuscular stimulators and implantable cardiac stimulators such as pacemakers and defibrillators, including automatic implantable cardioverter defibrillators (AICD), and provides enhanced noise identification for the proper response of such devices when exposed to various sources of interference.

BACKGROUND OF THE INVENTION

The performance of implantable medical devices sometimes suffers due to interference caused by electromagnetic noise. In implantable pacemakers and defibrillators, for example, such interference may cause the device to operate so as to put the patient's life at risk. For example, demodulated electromagnetic noise may cause inhibition of a pacemaker in a pacemaker-dependent patient, or may be recognized as an arrhythmia by a defibrillator, causing it to inappropriately shock the patient. Sources of electromagnetic interference (EMI) are common, and cannot always be avoided by patients with pacemakers or implantable defibrillators, for example. Some examples of such sources of interference are anti-theft article surveillance devices in stores, cellular telephones, power transformers, welding equipment, and certain medical equipment such as magnetic neuromuscular stimulators, diathermy instruments, electro surgery devices and magnetic resonance imaging (MRI) units.

Electromagnetic interference may enter an implantable pacing or defibrillator device either directly, appearing on the sensitive electronic circuitry through electromagnetic induction for which the typical titanium casing of the device does not provide sufficient shielding, or indirectly through the electrodes or leads to the device, acting as antennae, with high frequency noise bypassing the high frequency noise protection circuits by taking erratic pathways. Although pacemaker and defibrillator circuits are designed to reject unwanted frequencies, it is difficult, if not impossible, to reject interference signals having the same or similar characteristics as the signals produced by the heart. In such cases, even specialized noise detection circuitry based on repetition rate discrimination may be fooled by EMI.

It is therefore advantageous and desirable to provide an independent means for the detection and confirmation of the presence of near-field electromagnetic noise in the management of interference conditions in implantable cardiac medical devices. The present invention provides such an independent means, using a magnetically-coupled circuit, for example, for the wideband detection and confirmation of near-field electromagnetic noise that may be induced directly or indirectly into the circuitry of an implantable cardiac stimulator, with the EMI detection and confirmation circuitry of the present invention unrelated to sensing circuitry of the implantable medical device.

U.S. Pat. No. 5,383,912, issued Jan. 24, 1995, and assigned to the assignee of the present invention, discloses a method by which an external device communicates to an implantable medical device by sending to the antenna of the implantable device electromagnetic energy which is detected by a non-linear device, such as a diode, and stored as electrostatic energy. After a delay period representing data to be communicated, the stored energy is released and transmitted by way of the antenna as electromagnetic energy back to the external device. U.S. Pat. No. 5,383,912 shows one possible form of antenna circuit with which the present invention may be employed.

While embodiments of the present invention are presented herein in the context of implantable medical devices such as cardiac stimulators, the term "medical device" as used herein is intended to include any type of instrumentation that is implantable within a living site; the term "patient" as used herein is intended to include any type of living being, both human and nonhuman. The present invention is therefore applicable to any type of instrumentation that is implantable within any type of living being.

SUMMARY OF THE INVENTION

The present invention provides apparatus and method for detecting the presence of electromagnetic interference in an implantable medical device, independent of other circuitry of the device, and signaling the device of the presence of interference so that appropriate steps may be taken in response.

An electromagnetic interference detector according to the present invention utilizes an antenna that may be the antenna utilized by a telemetry circuitry of the medical device, or which may be dedicated to EMI reception. In the latter case, the antenna of the detector may be a coil within the casing of the device, such as a printed coil, a ferrite core coil or an air core coil, for example, or the antenna of the detector may extend beyond the metal case into the plastic header of the medical device so that the antenna is exposed to the electrical component of the electromagnetic interference and not just to the magnetic flux of the interference inside the case. Another alternative antenna for use by a detector according to the present invention is one or more leads between the medical device and the patient.

Signal processing circuitry is provided to process received and detected interference signals and provide a signal to the medical device depending on the presence of interference. The signal processing circuitry may include a threshold detector that selects those portions of the detected interference signals that are above a designated threshold value and provides a signal to the medical device indicating whether interference above the threshold value is present. The signal processing circuitry may include an analog-to-digital converter which converts the detected interference signals to digital form and provides signals to the medical device indicating the strength of interference detected.

The signal processing circuitry may include circuitry for comparing detected interference with a signal of physiological origin, for example, received by the medical device from the patient by way of a lead, such as circuitry for sampling the interference and the signal from the lead, for example, threshold detectors for selecting those portions of the interference and the signal from the lead that are above a designated threshold value, and a coincidence detector for comparing the portions of the interference and the signal from the lead that are above the designated threshold value and providing a signal to the medical device indicating whether a coincidence exists between the compared portions of the interference and the signal from the lead. When used, sampling circuitry may include two amplifiers that sample the interference signal and the signal from the lead, respectively, and, whenever a sampled signal circuit is used, a timing circuit directs the sampling by the two amplifiers to occur at the same rate and in unison.

In a method of the invention an electromagnetic interference detector is provided that is independent of the circuitry of the medical device. Interference signals are received on the antenna of a receiver and detected, then processed to provide a signal to the medical device depending on the presence of interference. The antenna may be provided as a system of multiple coils oriented in different directions Processing the interference signals may include comparing them to a designated threshold, and the step of providing a signal to the medical device that indicates whether interference above the threshold is present. Processing the interference signals may include converting them to digital form from analog form, and providing a signal to the medical device that indicates the strength of interference detected.

Processing the interference signals and providing a signal to the medical device may include sampling detected interference and sampling a physiological signal from the patient at the same sampling rate and in unison with the sampling of the interference, comparing the sampled interference and the sampled physiological signal from the patient with a designated threshold value and selecting those portions of the sampled interference and the signal from the patient that are above the designated threshold value, and comparing the portions of the interference and the physiological signal from the patient that are above the designated threshold value and providing a signal to the medical device indicating whether a coincidence exists between the compared portions of the interference and the physiological signal from the patient.

DETAILED DESCRIPTIONS OF THE PRESENTLY PREFERRED EMBODIMENTS

Figure 1:
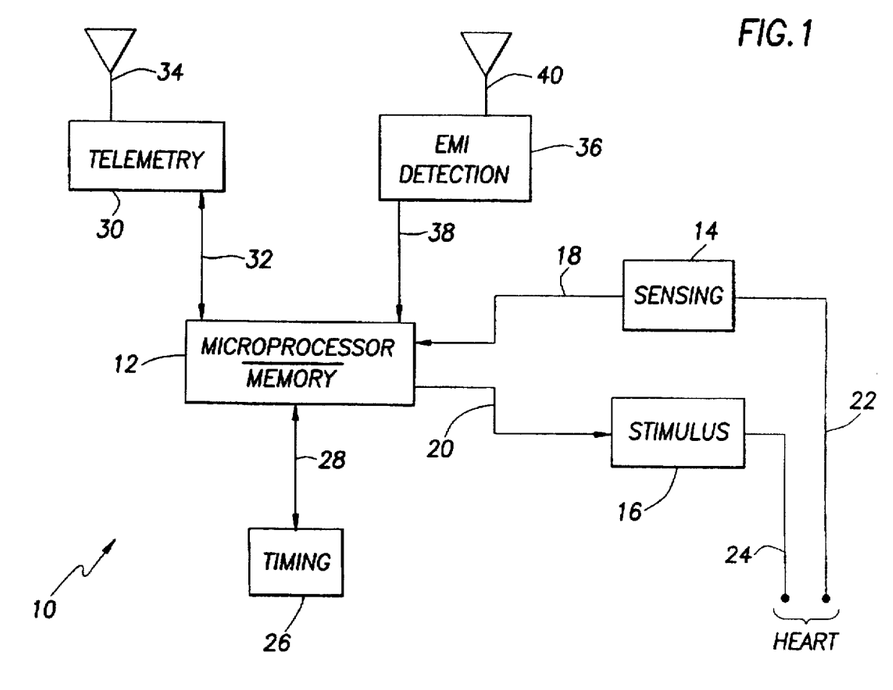
FIG. 1 is a block diagram of an implantable cardiac stimulator incorporating an electromagnetic noise detector according to the present invention.

A noise detector according to the present invention may be utilized in conjunction with any type of implantable medical device, including, but not limited to, neuromuscular stimulators and cardiac stimulators, such as pacemakers and defibrillators, and implantable drug delivery devices, for example. To this end, the present invention is shown in FIG. 1 included in a generic implantable cardiac stimulator which represents all forms of such devices, for purposes of illustration rather than limitation. Further, the noise detector of the present invention is indicated in FIG. 1 schematically only, and is intended to represent therein the present invention in general, as well as the several preferred embodiments of the present invention discussed more fully below.

In FIG. 1 an implantable cardiac stimulator is shown generally at 10, and includes all of the components of any such device. A microprocessor and memory 12 provides control and computational facilities for the device 10, as well as memory capability. Memory for the device 10 can be provided in whole or in part in a section separate from the microprocessor. Also, it will be appreciated that other forms of circuitry, such as analog or discrete digital circuitry, can be used in place of the microprocessor 12.

Sensing circuitry 14 and stimulus circuitry 16 are connected to the microprocessor and memory 12 by lines 18 and 20, respectively. The sensing circuitry 14 may represent amplifier sections for atrial sensing and/or ventricular sensing, according to the specific form the device 10 assumes. Likewise, the stimulus circuitry 16 may be of various forms, depending on the nature of the device 10. For example, if the device 10 is a pacemaker, the stimulus circuitry 16 may be an atrial pacing signal generator, or may be a ventricular pacing signal generator, or may represent both atrial and ventricular pacing signal generators. If the device 10 is a defibrillator, the stimulus circuitry 16 may include a high voltage generator for producing shock signals utilized to defibrillate the heart of the patient. In a combination system including a pacemaker and a defibrillator, the stimulus circuitry 16 may represent multiple generators for producing the various stimulation signals required to shock or pace the heart, for example.

The sensing circuitry 14 is shown connected to the heart of the patient, in whom the device 10 is implanted, by a lead system 22 that ends in one or more electrodes appropriate for the device 10. For example, if the device 10 is a dual chamber pacemaker that senses the conditions in both atrial and ventricular chambers, the lead system 22 may include two lines ending in two electrodes, with one electrode positioned in an atrial chamber and the other electrode positioned in a ventricular chamber. Otherwise, if the device 10 is to sense heart function in only one chamber, the lead system 22 may end in a single electrode appropriately positioned relative to the heart. In any event, the sensing circuitry 14 detects signals in the designated area or areas of the heart by way of the lead system 22 as indicative of the heart function, amplifies the sensed signals and conveys them to the microprocessor and memory section 12 over the line 18.

It will be appreciated that heart signal sensors are not the only type of sensors utilized by implantable medical devices. Other types of sensors include oxygen sensors, for example, and the present invention may be utilized with medical devices employing such sensors as well.

The stimulus circuitry 16 is shown connected to the heart of the patient by a lead system 24 that ends in one or more electrodes appropriate for the device 10. For example, if the device 10 is a defibrillator, the lead system 24 may include multiple leads and high voltage patch electrodes for applying shock signals to the heart. If the device 10 is a combination cardiac stimulator, the lead system 24 may represent a defibrillator electrode system as well as a pacer electrode system. In the event that the device 10 is a pacemaker, the two lead systems 22 and 24 may be combined to provide electrodes used for both acquiring sensed signals from the heart to the sensing circuitry 14 as well as conveying pacing signals from the stimulus circuitry 16 to the selected one or more chambers of the heart.

Timing circuitry 26 is shown connected to the microprocessor and memory section 12 by a line 28 to provide timing signals necessary for the operation of the device 10. For example, the liming circuitry 26 may provide pacing interval liming for a pacemaker, and a clock for any other required timing signals for the operation of the device. The line 28 is shown representing a capability for timing signals to be conveyed to the microprocessor 12, and a capability for triggering signals, for example, to be conveyed from the microprocessor to the timing circuitry.

A telemetry section 30 is connected to the microprocessor and memory 12 by a line 32, and is equipped with an antenna 34. The telemetry system 30 may receive information from the microprocessor 12 concerning the functioning of the heart as well as the condition of the device 10, for example, by means of the line 32, and transmit such information over the antenna 34 to an appropriate receiver outside the patient. Also, the telemetry system 30 may receive programming and commands from an attending physician, for example, by way of appropriate communication signals received over the antenna 34, and convey such information over the line 32 to the microprocessor and memory 12. In this way, various liming controls and thresholds may be adjusted, for example, to appropriately control the operation and responses of the device 10 to meet the needs of the patient. Typically, the telemetry antenna 34 takes the form of a multiturn coil inside the housing, or case, of the device 10.

In practice, EMI that is a concern addressed by the present application may be received by leads to the heart such as the lead systems 22 and 24 of the device 10, and conveyed to the circuitry thereof. Also, EMI may penetrate the case containing the device 10, although such case is typically constructed of titanium and hermetically sealed. In particular, such noise invading the case may be magnetically induced on the coil antenna 34, for example, and thereby introduced into the circuitry of the device 10. The present invention provides a technique for detecting such EMI that may be impressed on the circuitry of the device 10 regardless of the avenue by which the noise has reached the circuitry, and for identifying the noise as such to the device which can then respond so as to not endanger or unnecessarily stress the patient.

A noise detector according m the present invention is shown in FIG. 1 to include an EMI detection section 36, coupled to the microprocessor and memory 12 by a line 38, and equipped with an antenna 40. Details of the construction and operation of noise detectors according to the present invention are provided below. In general, the detector circuitry 36 in FIG. 1 receives EMI by means of the antenna 40. As explained more fully below, the antenna 40 of the noise detector may be the same as the antenna 34 of the telemetry section or may be a separate, dedicated antenna, or may be a lead in one or the other of the lead systems, 22 or 24. However, beyond such antenna provisions, the circuitry of a noise detector of the present invention functions independently of other circuitry of the implantable medical device with which the noise detector is used, and particularly is independent of the circuitry of the medical device used to detect and process sensed signals from the patient, whether such signals are physiological, that is, that relate to physiological functions of the patient, or nonphysiological signals, such as signals indicating movement by the patient.

Figure 2:
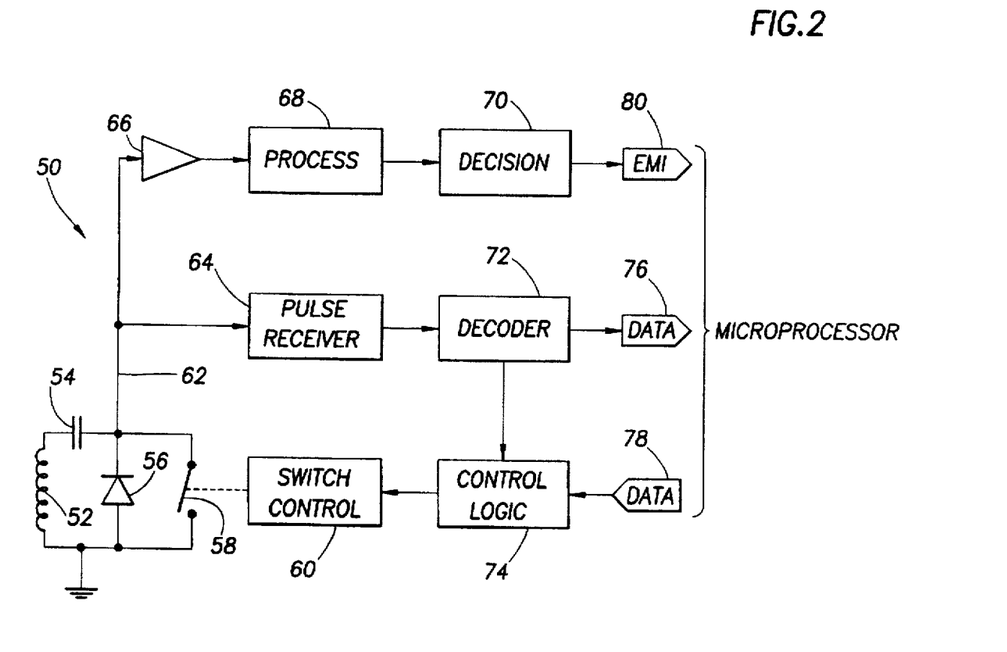
FIG. 2 is a block diagram of a preferred embodiment of a noise detector according to the present invention, utilizing the telemetry antenna of an implantable medical device to detect electromagnetic noise.

In one form of a preferred embodiment of the present invention the antenna of an implantable medical device that is used for communications and telemetry is also used as part of a circuit to detect the presence of electromagnetic fields that may cause the device to malfunction, or that may adversely influence the behavior of the device. In particular, the circuit associated with the telemetry coil antenna is enhanced to enable the detection of wideband electromagnetic signals, such as with components in a range from 0.5 HZ to 2 GHZ, even of relatively low level. In the event that electromagnetic noise signals are induced in the telemetry antenna, they are detected and appropriately processed, resulting in the generation of a warning signal to alert the microprocessor of the presence of EMI, for example. Such EMI processing may include, but is not limited to, amplification, filtering, demodulation, integration and counting, for example. FIG. 2 is a block diagram of a form of telemetry circuitry, and of an embodiment of noise detection and processing circuitry according to the present invention, all shown generally at 50, for use in an implantable medical device such as a cardiac stimulator, for example. It is understood, however, that a noise detector according to the present invention may utilize any appropriate form of receiver circuit, and any appropriate form of antenna.

Telemetry circuitry and noise detection circuitry, according to the present invention, shown generally at 50 in FIG. 2 include an antenna circuit comprising the multiturn coil antenna 52 of the cardiac stimulator as described above, a capacitor 54, and a diode 56. A switch 58 is positioned in parallel with the diode 56, and is associated with a switch control circuit 60 that selectively closes the switch to effect transmission of data from the cardiac stimulator over the antenna 52 to outside the body of the patient. A connection 62 extends from the junction between the capacitor 54 and the diode 56 in parallel with the switch 60, to a pulse receiver 64 of the telemetry and communication circuit as well as an amplifier 66 in the noise detection section of the circuit 50. The output from the amplifier 66 is communicated to signal processing circuitry 68, and the processed signals from that circuitry are communicated to decision circuitry 70. Output from the pulse receiver 64 is communicated to a decoder 72, which has an output connected to a transmitter control logic circuit 74. The output from the logic circuit 74 signals the switch control circuit 60.

The noise detection section of the cardiac stimulator circuitry comprises circuits 66–70, and shares the use of the antenna circuit, comprising parts 52–56, with the remainder of the telemetry and communication section comprising circuits 60, 64, 72 and 74, but is otherwise independent of the telemetry and communication section in construction and function.

The operation of the antenna circuit 52–56, with the switch 58, in the receipt of communications to the cardiac stimulator, and in the transmission of data from the cardiac stimulator, is discussed in U.S. Pat. No. 5,383,912. In that context, communication between the cardiac stimulator and an external receiver/transmitter through the antenna circuit 52–56 and the switch 58 is by way of pulses of electromagnetic energy. The telemetry and communication section, shown generally here in FIG. 2, communicates with additional circuitry of the implantable device, such as sensing and stimulus circuitry 14 and 16, respectively, and a microprocessor such as 12, as shown in FIG. 1, for example, sending data to the additional circuitry at 76 and receiving data therefrom at 78 in FIG. 2.

With the switch 58 open, electromagnetic energy pulses from an external transmitter are received by the antenna coil 52. The resulting transient electric current produced in the antenna 52 is converted with the use of the diode 56 as a non-linear component to a non-zero average electric current which charges the capacitor 54 with electrostatic energy. The receipt of the electromagnetic pulses is sensed by the pulse receiver 64 by means of an analog signal along line 62. Upon detection of the receipt of an electromagnetic pulse, the pulse receiver 64 communicates a binary pulse to the decoder 72. The incoming pulse signals to the antenna 52 from an external transmitter may be in the form of pulse trains that are pulse-position modulated. The decoder tracks the timing of the pulses and communicates binary signals as data out to the microprocessor and other circuitry of the cardiac stimulator at 76.

The cardiac stimulator generates selected information signals in binary form regarding the condition and functioning of the heart of the patient, and the condition of the device itself, and conveys these signals as data 78 to the transmitter control logic circuit 74. An output from the decoder circuit 72 provides information of the timing of the incoming pulse signals from the external transmitter to the logic circuit 74 so that the transmission of signal pulses by the cardiac stimulator to the external receiver may be appropriately coordinated with the incoming pulse timing. The time-placement of the signal pulses to be transmitted by the cardiac stimulator, with the incoming pulses, carries the data regarding the condition and functioning of the patient heart and of the cardiac stimulator to the external receiver. The logic circuit 74 sends a pulse to the switch control circuit 60 each time an electromagnetic pulse is to be transmitted over the antenna 52 to the external receiver, and the control circuit closes switch 58 in response for the time dictated by the signal from the logic circuit. Closing the switch 58 allows a discharge of the energy stored in the capacitor 54 by the original pulse or pulses sent to the antenna 52 from the external transmitter, with the result that current flows through the antenna for the time required to produce an electromagnetic pulse according to the pulse conveyed by the logic circuit 74. In this way, the cardiac stimulator uses energy received from an external transmitter for the production of electromagnetic signals transmitted by the cardiac stimulator to an external receiver.

In addition-to the electromagnetic signals from the external transmitter, EMI may be induced on the antenna 52 and communicated to the pulse receiver 64, there to confuse the information pulse train signals, or to be interpreted as possible command signals, for example. By further processing the signals received on the antenna 52 from the external transmitter and detected, it is possible to detect the presence of EMI and also maintain the full functionality of the telemetry system. The same signals induced on the coil antenna 52 that are communicated through the diode 56 to the pulse receiver 64 are also communicated to the amplifier 66. The analog signals from the antenna section 52–56 are amplified at 66, and the amplified signals selectively processed at 68 to detect any EMI present. A decision is made at 70 based on the presence and strength of EMI, and an appropriate signal is communicated at 80 to the microprocessor of the implantable device. The processing and handling of signals as at 68 and 70 are discussed in detail below.

Although a particular type of telemetry and communication section is presented herein for purposes of illustration only, a noise detector according to the present invention may be employed with any type of telemetry system consistent with the requirements of an implantable medical device.

Figure 3:
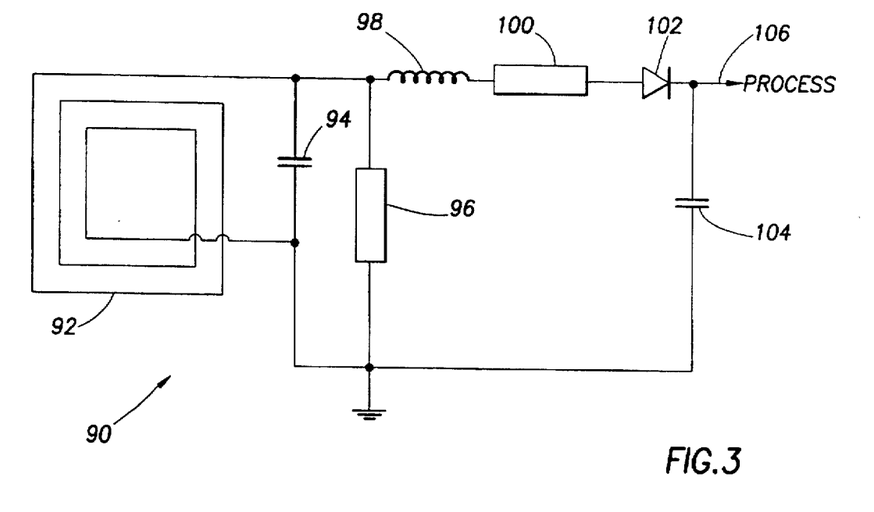
FIG. 3 is a schematic diagram of another preferred embodiment of a noise detector according to the present invention, utilizing a dedicated antenna.

Another preferred embodiment of a noise detector according to the present invention utilizes an antenna separate from the telemetry antenna of the implantable medical device in which the noise detector is employed. A detection circuit using one or more zero-bias Schottky detector diodes, such as diodes in the HSMS-285X Series of Hewlett-Packard Company, performs detection of wideband electromagnetic noise signals with virtually no power consumption from the power source of the implantable device. FIG. 3 illustrates such a noise detector, shown generally at 90, including a wideband antenna circuit, comprising a dedicated coil antenna 92 and a capacitor 94, and an impedance-matching network. The antenna 92 is a multiturn, miniature coil which can be printed by lithographic techniques, for example, on one of the wiring layers of the ceramic substrate on which circuitry of the implantable medical device is constructed.

A microstrip transmission line 96 of the impedance-matching network is in parallel with the coil antenna 92 and the capacitor 94, and an inductor 98 is connected to the junction of those three components. A second microstrip transmission line 100 is connected to the other end of the inductor 98, and a zero-bias Schottky diode 102, such as HSMS-2850, is connected to this latter transmission line. An integrating capacitor 104 is connected between the output 106 of the diode 102 and ground. The impedance-matching network comprises parts 96–102. Output 106 from the circuit 90 is communicated to processing circuitry, as discussed below, for determining the nature of the EMI signals and signaling the microprocessor of the implantable medical device accordingly.

The network 96–102, along with the antenna circuit 92,94, can be tuned to vary the frequency response of the detector 90, particularly by selecting the capacitor 94, the inductor 98, and the two transmission lines 96 and 100. For example, the circuit 90 may be tuned to have high sensitivity at specific frequencies, such as the frequency range at which digital cellular phones operate. Also, variation of the frequency response alters the bandwidth within which the detector 90 is effective. In general, wideband EMI detectors such as the detector 90 of FIG. 3 may be constructed to take advantage of the high detection sensitivity of zero-bias Schottky diodes. Specifications and uses of the HSMS-285X Series of diodes, including power transfer and communications methods, are reported in "Surface Mount Zero Bias Schottky Detector Diodes Technical Data" publication #5963-2333E of Hewlett-Packard Company, 1994, which discloses the following detection sensitivities for those diodes:

40 mV/μW at 915 MHz, 30 mV/μW at 2.45 GHz, and 22 mV/μW at 5.80 GHz.

Figure 4:
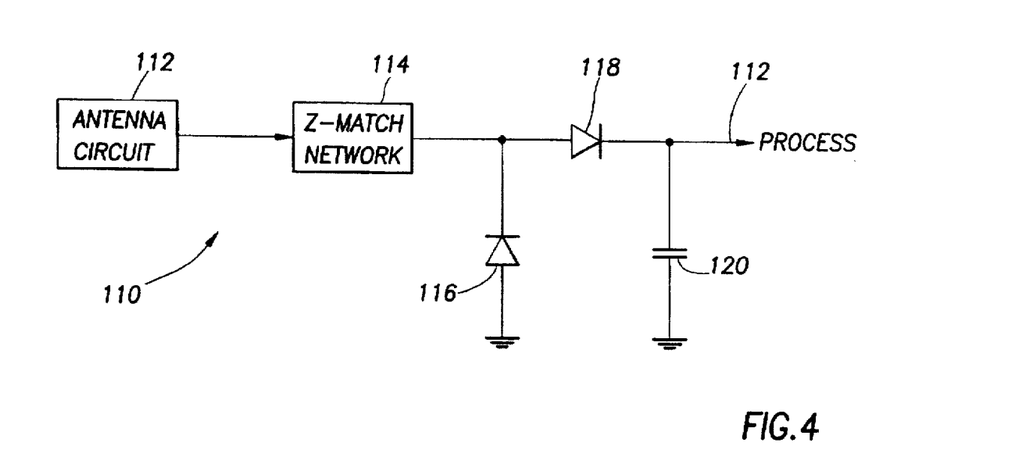
FIG. 4 is a schematic diagram of still another embodiment of a noise detector according to the present invention, providing fullwave rectification of the EMI signal.

FIG. 4 shows a detector circuit 110 for use in an implantable medical device, including a tuned antenna circuit 112 having an antenna of any type, and an impedance-matching network 114. Output from the network 114 is communicated to a fullwave rectifier, comprising two zero-bias Schottky diodes 116 and 118, such as HSMS-2852 diodes. The rectifier 116,118 is followed by an integrating capacitor 120. Output from the detector 110 is communicated at 122 for further processing.

Where exposure of zero-bias Schottky diodes to very high RF fields may cause power coupling into the Schottky diode rectifier, such power coupling may be prevented by use of a PIN diode pair such as a HSMS-3822.

Figure 5:
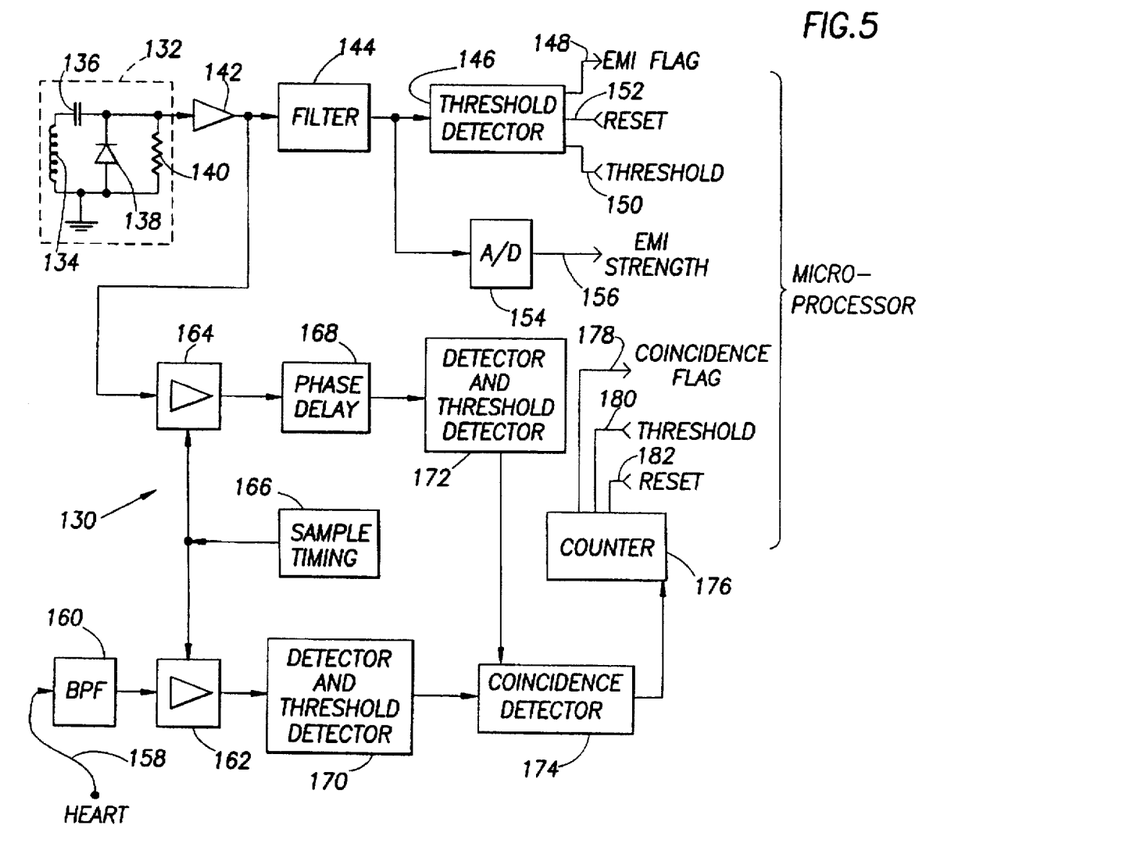
FIG. 5 is a schematic diagram of a noise detector according to the present invention, showing details of signal processing circuitry.

Signal processing circuitry for an EMI detector according to the present invention may implement a number of different functions. FIG. 5 shows a noise detector according to the present invention with signal processing circuitry, and sensing circuitry of an associated implantable cardiac stimulator, for example, all shown generally at 130, for providing several options to the cardiac stimulator for utilizing detected EMI signals from the noise detector.

An electromagnetic signal receiver is indicated in FIG. 5 within the dashed-line border 132, and includes a coil antenna 134, a storage capacitor 136, a detector diode 138 and a resistor 140. A signal rectified by the diode 138 is demodulated by the low pass filter formed by the capacitor 136 and the resistor 140, and is output to an amplifier 142. The resistance 140 could be the input impedance of the amplifier 142. The signal processing circuitry illustrated in FIG. 5 could be utilized with any type of electromagnetic signal receiver, using the telemetry antenna of the implantable device or another antenna of any suitable type, and the signal receiver 132 is representative of any type of such circuit.

The rectified and demodulated noise signal is amplified by the amplifier 142 and appropriately filtered at 144. In one type of signal processing the output of the filter 144 is used by decision circuitry 146 comprising a comparator and logic latching circuitry to determine whether the detected electromagnetic field exceeds a certain programmable threshold level. The threshold detector 146 may measure the noise signal amplitude, duration, repetition rate, frequency, or any other feature of the signal. As used herein, therefore, the terms "level", "threshold level" and "threshold value" are understood to refer to any feature of a signal, and a threshold detector such as 146 compares such a feature of the signal input thereto to a designated level, or quantity, etc., of the feature. The threshold detector 146 generates an "EMI present" flag at 148 to the microprocessor of the implantable device whenever the threshold is exceeded. The presence of such an electromagnetic field may also be causing the sensing circuitry of the implantable device to be operating incorrectly. The microprocessor is alerted by the "EMI present" flag of this possibility, and can then take appropriate steps to insure the safety of the patient. The threshold detector 146 receives the threshold level setting and a latch reset signal from the microprocessor at 150 and 152, respectively.

The analog signal output from the filter 144 may also be processed to allow the microprocessor to quantify the strength of the EMI field, and to construct a log, or profile, of the exposure of the implantable device to EMI over a selected time period, for example. The filtered signal is communicated to an analog-to-digital converter 154 whose digital output signal is communicated to the microprocessor as EMI presence and strength data, to be collected and stored, as a function of time. The accumulation of such stored data may be conducted over a selected time period, such as a day, for example. The stored data may then be downloaded on command from the implantable medical device to an external receiver by way of the telemetry system of the implantable device as a profile of peak exposure to EMI throughout the selected time period, with the data parceled in short time periods, such as of fifteen minutes each, for example.

Figure 6:
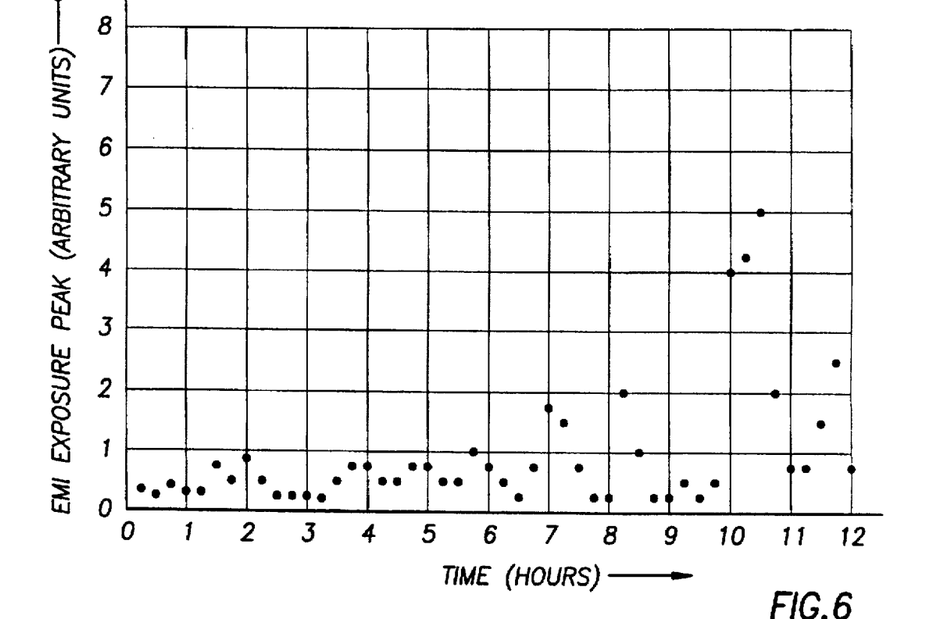
FIG. 6 is a graph of a hypothetical twelve-hour peak EMI exposure profile for a patient having an implantable medical device with a noise detector according to the present invention.

FIG. 6 illustrates such a profile of EMI experience for a hypothetical case, including peak exposure readings every fifteen minutes for a twelve hour period. The exposure data may be provided as average EMI values over each fifteen minute measuring period, or as peak EMI values over each such measuring period. Such an EMI exposure profile would provide the physician treating the patient who is the recipient of the implantable device with valuable information for programming the sensing and response parameters of the implantable device, for example. Further, correlating the time scale of the profile with actual behavior of the patient during the selected data gathering time period would provide information about areas or activities that should be avoided during the patient's daily life.

An EMI exposure profile such as shown in FIG. 6 may also be used in conjunction with a patient activity profile constructed from actual measurements of the activity. For example, the implantable medical device with which the detector of the present invention is used may include an accelerometer which senses movements by the patient and provides data signals accordingly. Processing the accelerometer data signals can provide an activity time profile, say for the same time period as an EMI exposure profile as shown in FIG. 6 is obtained for the same patient. Additionally, various physiological parameters of the patient, such as heart beat, blood pressure, oxygen consumption, etc. may be sensed over the same time period and graphs obtained similar to the EMI exposure profile and the patient activity profile, for example. In this way, valuable information relative to the patient's health and exposure to possible danger may be obtained and studied toward treating the patient and/or reducing the patient's exposure to dangerous circumstances.

Another variation in the formation and use of an EMI exposure profile such as illustrated in FIG. 6, as well as profiles of measured patient activity and physiological parameters, for example, involves recording the data on which such a profile is constructed only upon the occurrence of some specified event. For example, the EMI peak information obtained with the use of the output 156 of the A/D converter 154 can be free running in general, and frozen, or saved, only when some event occurs, such as the EMI strength exceeding a selected threshold. Then, the microprocessor can save the EMI data for the next twelve hours, for example, and construct a profile that is expressible as a graph as shown in FIG. 6, for example.

Alternatively, EMI data from the output 156 can be saved continuously, and, after startup, every twelve hours the data for the twelve hour period beginning twenty-four hours ago and ending twelve hours ago erased. Then, when a triggering event occurs, such as EMI exceeding the selected threshold value, EMI data for the twelve hour time period immediately preceding the event can be saved along with data for the next twelve hour period following the event and presented as a twenty-four hour EMI exposure profile, for example. Profiles of patient activity and other parameters for the same time periods may be obtained as discussed above for comparison and analysis in conjunction with the use of EMI exposure profiles. Variations of such save-and-record profile patterns can be utilized with noise detectors according to the present invention.

Other events which may be utilized to trigger collecting EMI exposure data and constructing an exposure profile, for example, would include the occurrence of a specified number of EMI signals above a selected threshold within a given period of time. For example, if the patient experiences exposure to EMI signals above a designated level ten times in a twenty minute period, the save-and-record profile process might be triggered. The triggering signal may be initiated by the behavior of some other parameter, including a physiological parameter of the patient, such as a rise in blood pressure above a specified value.

The patient may also choose to initiate saving and collecting EMI exposure data into a profile as graphed in FIG.

6, for example. U.S. Pat. No. 5,304,206, issued Apr. 19, 1994, discloses an implantable neurostimulator that can be initiated manually by the patient applying selected pressure to the implanted device.

Still another implementation of the signal processing circuitry of an EMI detector according to the present invention involves the use of a coincidence detector to constantly monitor for coincidence of sensed events with those coming from the EMI detector. In FIG. 5 a sensing lead 158 extends from a bandpass filter 160 to the patient's heart to acquire heart signals, such as atrial sense signals, for example. The lead 158 may also convey sensed signals to sensing circuitry (not shown) of the cardiac stimulator as discussed above in connection with FIG. 1, for example. The output from the filter 160 is communicated to an amplifier 162. The amplified EMI signal from the amplifier 142 is communicated to another amplifier 164. The analog signals input to the two amplifiers 162 and 164 are suitably amplified by the respective amplifiers. The amplifier circuits 162 and 164 may also include signal filtering circuitry. Also, the amplifiers 162 and 164 may be linear amplifiers with filters, or they may be switched-capacitor amplifiers, for example. If sampled signal amplifiers or filters are used, the sampling rate is determined by a common timing signal from a common timing circuit 166 to insure that both amplifiers are sampling at the same rate and in unison.

The signal output from the amplifier 164 is communicated to a phase delay circuit 168 which shifts the phase of the signal to cancel the effect of any prior phase shifting experienced by the detected EMI, such as due to low pass filtering in the receiver circuit 132, for example.

The output signals from the amplifier 162 and the phase delay circuit 168 are communicated to sense and threshold detector circuits 170 and 172, respectively. In each of the circuits 170 and 172 the input signal is rectified and compared to the same predetermined, programmable threshold, utilizing a comparator. The feature of the signals compared to a threshold in the detectors 170 and 172 may be any signal feature, as discussed above in connection with the threshold detector 146. Those portions of the signals above the threshold level are output from the detector circuit 170 to one input of a coincidence detector 174, and from the detector circuit 172 to another input of the same coincidence detector. The coincidence detector 174 compares same-time signal samples, for example, from the detected EMI and the sensed signals obtained by way of the lead 158 to determine whether these two signals exhibit coincidence. If coincidence is noted between the EMI signal and the sensed signal from the lead 158, for example, the coincidence detector 174 communicates a signal to a coincidence counter 176. The output signal from the coincidence detector 174 to the counter 176 indicates the presence of coincidence detected between the two input signals from the detectors 170 and 172. The counter 176 determines the rate at which the presence of coincidences are signaled to it by the detector 174, as well as the duration of each such coincidence. When the counter 176 determines that a coincidence exists between the detected EMI and the sensed signal from the lead 158, either in duration beyond a specified threshold time period, or in repetition rate, the counter produces a coincidence flag signal at 178 to the microprocessor of the medical device. The counter 176 receives the threshold time, or repetition rate, setting and a latch reset signal from the microprocessor at 180 and 182, respectively.

The nature of the sensor associated with the lead 158 in FIG. 5 will depend on the type of implantable medical device with which the noise detector circuitry of FIG. 5 is utilized. In general, any type of patient parameter, whether physiological or not, may be intended to be sensed by way of the lead 158, such as patient movement, blood pressure, etc.

Regardless of the nature of the parameter to be sensed by the sensor associated with the lead 158 in FIG. 5, the actual signal conveyed by that lead to the filter 160 may be anywhere from 0% noise to 100% noise. In the latter case, of course, the signal does not include any patient parameter information, there having been no patient-related event to sense, either physiological or not, and the signal on the lead will most likely exhibit coincidence with the EMI signal conveyed to the amplifier 164, for example. However, even if the signal to the filter 160 is only partially noise, coincidence with the detected EMI may be detected at 174.

Figure 7:
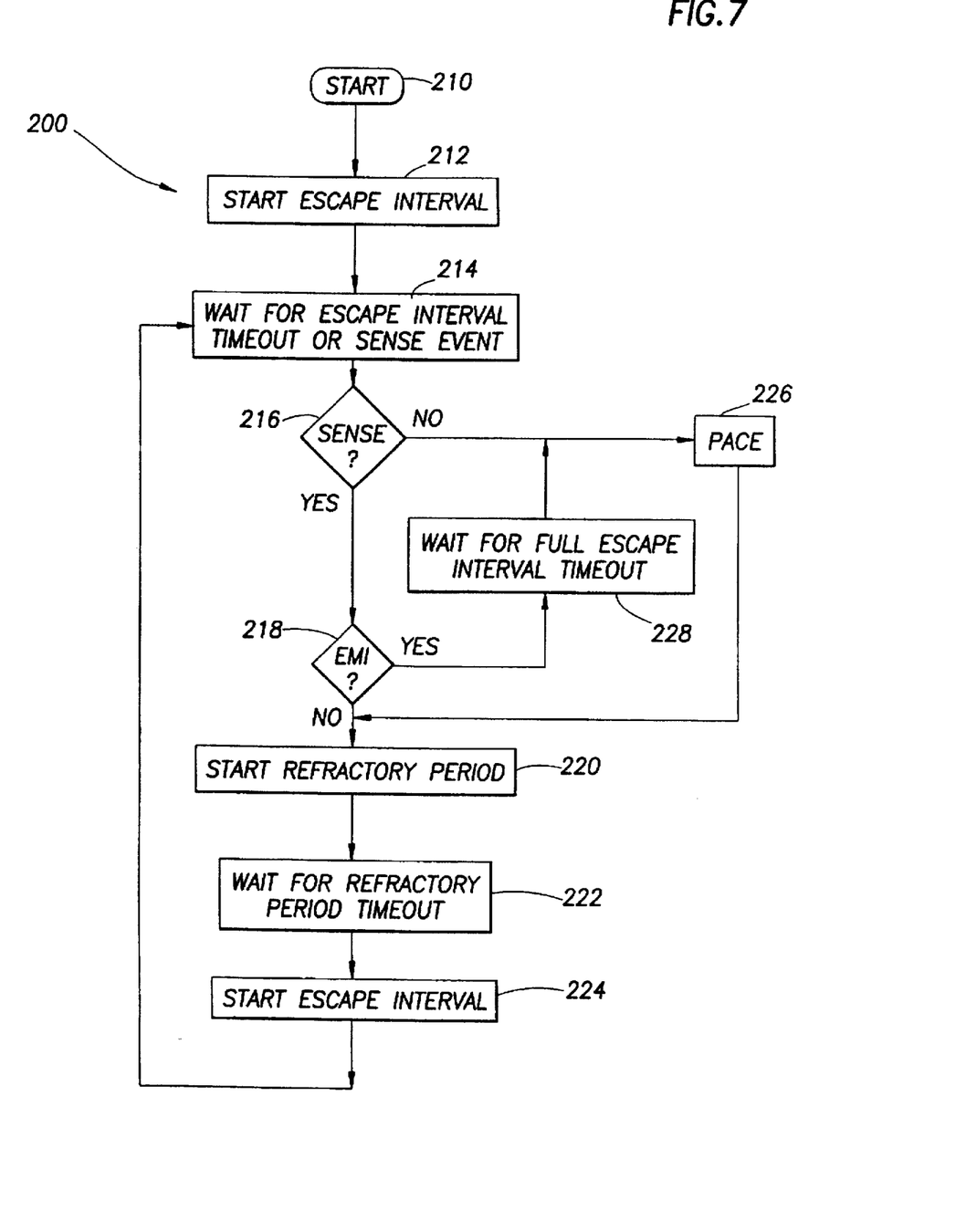
FIG. 7 is a flowchart of process steps for use in an implantable cardiac stimulator in conjunction with a noise detector according to the present invention.

The various signal processing modes for utilizing detected EMI in an implantable medical device employing a noise detector according to the present invention, as discussed above in conjunction with FIGS. 5 and 6, for example, may be exploited in various ways by the implantable device. FIG. 7 illustrates one such method, indicated generally at 200, of exploiting the information obtained and forwarded to the microprocessor of an implantable medical device from an EMI detector as shown in FIG. 5, for example.

In the method 200 of FIG. 7 the microprocessor of a demand pacemaker, for example, responds to the message that EMI has been detected in the same manner that it would respond if it sensed that the heart of the patient has failed to perform an expected event, that is, by producing a pacing signal to pump the chamber in which heart signals are being sensed, for example. Upon the start 210 of the illustrated process 200 the microprocessor initiates an escape interval at 212, that is, a time interval during which the pacemaker waits for the heart to perform an event, such as producing a pacing signal, for the pacemaker to sense and during which the pacemaker will not send a pacing signal to the heart. At 214 the pacemaker waits for the escape interval to expire, or the pacemaker to sense an event at the heart, whichever occurs first. The microprocessor inquires at 216 whether a heart event was sensed by the expiration of the escape interval. If the answer is affirmative, the microprocessor proceeds from 216 to determine at 218 whether it has received an "EMI present" flag, or an EMI coincidence flag, for example, from the noise detector of the present invention during the time period since the start of the escape interval at 212. If no indication of EMI was received during that time, the microprocessor starts a refractory time period at 220, usually of a few millisecond duration, during which the pacemaker is blind to any heart activity. The microprocessor waits for the expiration of the refractory period at 222. A new escape time interval is initiated at the end of the refractory period at 224, and the process returns to step 214 to continue. As an alternative, the new escape interval may be started with the start of the refractory period at 220, provided the new escape time interval is extended by an amount equal to the length of the refractory time period.

If, at 216, the microprocessor determines that the pacemaker has not sensed a heart event by the expiration of the current escape interval, this circumstance is taken to mean the patient needs assistance so that the process proceeds to 226 wherein the pacemaker generates a single pulse to stimulate the heart. The process then moves to 220 to start a refractory period as discussed above, followed by the steps 222 and 224, with a subsequent return to 214 to continue the process. Again, if the pacemaker has not timely sensed a heart event as inquired at 216, a single stimulus pulse will be generated and transmitted to the heart at 226. Such single pulses will continue to be provided to the heart as long as step 216 is reached without a heart event being sensed during the then-current escape interval. This is the normal response of the pacemaker in question to a failure of the heart to maintain a proper rhythm of self-generated stimulus signals in the chamber at which the sensing electrode is situated.

As the process diagram 200 shows, whenever a heart event is not timely sensed, the microprocessor will cause the pacemaker to provide a stimulus pulse to the heart at 226, followed by steps 220–224, without inquiring at 218 whether EMI has been detected. As long as the heart is showing the need for assistance in the form of a stimulus signal, this normal operation of the pacemaker will be followed, regardless of the presence in the pacemaker of EMI; consequently, under such circumstances no inquiry need be made regarding the presence of EMI. However, if the pacemaker has received a sense signal indicating the timely generation of a heart signal by the heart itself, inquiry is made at 218 regarding the presence of EMI. Then, if EMI is not present, a conclusion is reached that the pacemaker is functioning properly and the sensed signal is a true indication of the occurrence of the heart event. However, if EMI is determined at 218 to be present, the microprocessor cannot know whether the signal sensed by the pacemaker was actually the result of a heart event or the result of EMI in the pacemaker electronics. As noted above, a sensed signal may include anywhere from 0% noise to 100% noise, and not include any signal sensed as a result of an actual heart event. Therefore, if EMI is determined at 218 to be present, the pacemaker proceeds as if the patient needed assistance. The pacemaker waits at 228 for the current escape time interval to be completed, if it has not yet been completed (since the microprocessor arrived at step 218 only because a sense signal was detected at 216 to have been received by or before the expiration of the escape interval), and generates a stimulus pulse at 226 followed by steps 220–224, etc.

The process steps 200 of FIG. 7 are only one example of utilization of a noise detector according to the present invention. Processes for other and more sophisticated implantable devices, utilizing noise detectors according to the present invention, are equally possible. Likewise, such processes may be provided in conjunction with any of the various techniques for processing the EMI signals, such as discussed in connection with FIG. 5, for example. The inquiry 218 in the process 200 as detailed in FIG. 7 may utilize an "EMI present" flag 148 as illustrated in FIG. 5, so that the presence of EMI above the selected threshold level set at 150 determines whether reversion to a specified "noise mode" by the pacemaker is appropriate. Also, the detection of a coincidence, or multiple coincidences, or coincidences above a certain time rate, at 178 in FIG. 5, for example, may be used to trigger the reversion to the specified "noise mode". Such a "noise mode" might be "V00", that is, ventricular stimulation, no atrial or ventricular sensing, and no atrial or ventricular inhibition or triggering, to achieve asynchronous ventricular pacing at a known rate, for example.

If the signal processing circuitry of a noise detector according to the present invention determines that a coincidence exists between sensed signals coming from the heart sensor lead of the implantable medical device, and EMI as detected by the noise detector, whether the coincidence is in time or frequency of the signals in question, the implantable device will not rely on the sensed signals as indicating actual heart events, and will provide safety pulses as described above until the circuitry determines that such a coincidence no longer exists. The detection of EMI in an implantable device showing the same frequency profile as sensed heart events is an indication that the sensed heart signals are most probably false, and due to interference from the noise rather than actual heart events. Consequently, such a coincidence is interpreted as indicating EMI induced confusion of the sensing circuitry, which can therefore not be relied on to reflect the true condition of the heart, and reversion to a specified "noise mode" is carried out to insure the well-being of the patient.

As shown in FIG. 5, both "EMI present" and EMI coincidence signal processing may be utilized in the same implantable cardiac stimulator, for example, with the stimulator safety pacing the patient's heart, for example, in response to a positive result for either type of processing of detected EMI signals. At the same time, a peak EMI exposure profile may also be obtained for the patient.

As noted above, the present invention may utilize various antenna configurations. EMI may penetrate the metal case of an implantable device by magnetic flux interaction with the circuitry, including whatever internal antenna may be utilized by the noise detector, for example. If the noise detector uses an internal coil antenna, the ability of the antenna to receive induced EMI may depend, to some extent, on the orientation of the coil of the antenna, with the response of the antenna being greatest when the plane along which the turns of the coil are positioned is perpendicular to the direction of the changing magnetic flux of the EMI. The response of an internal coil antenna of a noise detector may be maximized by providing coil turns that are effectively located in all possible plane orientations. This effect can be accomplished by using a three-dimensional coil antenna construction, for example.

Figure 8:
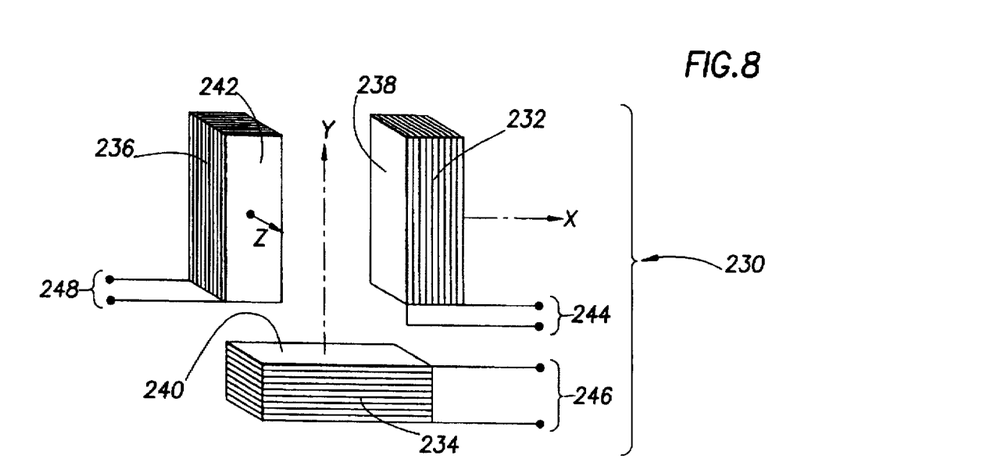
FIG. 8 is an illustration of an antenna system including three coils oriented mutually orthogonally for maximum directional noise responsiveness for use as part of a noise detector according to the present invention.

A three-dimensional coil antenna system for use in a noise detector according to the present invention is shown schematically generally at 230 in FIG. 8. The antenna system 230 includes three multiturn coils 232, 234 and 236, wound on separate ferrite cores 238, 240 and 242, respectively. The coils 232, 234 and 236 are oriented such that a plane defined by the turns of each coil is perpendicular to the direction of a different axis of an orthogonal axis system XYZ. Thus, coil 232 is perpendicular to the X axis, coil 234 is perpendicular to the Y axis, and coil 236 is perpendicular to the Z axis. Each coil is thus oriented to have maximum exposure to magnetic flux changes in one of the three orthogonal axis directions. Further, the ferrite cores 238, 240 and 242 enhance the signal induction on the respective coils due to exposure to changing magnetic flux, although the coils could be air-cored.

The three coils, providing received signals to three corresponding antenna circuits whose output is then combined, provide exposure to magnetic flux change induction in all directions. The coils 232, 234 and 236 feature lead lines 244, 246 and 248, respectively, to separate receiver circuits, for example. Thus, the orthogonal coil antennas can be combined to provide a single, all-directional noise antenna, by joining the received signals from the separate coils in the noise detector circuitry, for example.

The coils 232, 234 and 236 of the antenna system 230 may be positioned within the case of an implantable medical device at different locations, or at the same location where possible, for example. The cross-sectional area of the different coils may not be the same. For example, a coil oriented in the general plane of the relatively flat case of the implantable device may have a relatively large cross section compared to the cross sections of the other two coils. The responsiveness of the coils to induced noise signals may be equalized by appropriate variation in the respective circuitry for the three coils, or by varying the number of turns in the different coils, it being realized that the response of a coil to magnetic flux changes increases for an increase in the number of turns of the coil.

Two of the three coils 232–236 may be wound on a single ferrite core. For two such coils 232 and 234, for example, the core is generally in the form of a cross, which may be considered as formed by combining the two cores 238 and 240.

Another possible method for detecting the magnetic component of EMI is to use a solid state sensor capable of producing an electrical signal proportional to a time-varying magnetic field. The use of one such sensor is described in concurrently-filed U.S. patent application Ser. No. 08/475, 491 titled Apparatus and Method for the Control of an Implantable Medical Device. That application discloses a giant magnetoresistance ratio (GMR) sensor, within an implantable device's circuitry, that responds to the magnetic component of low frequency (<100 MHz) EMI fields. The antenna, rectification and filtering functions of a noise detector according to the present invention, as presented in any of the embodiments herein, for example, may thus be provided by a GMR sensor that is appropriately excited, and the signal of which is appropriately conditioned (for example, amplified and filtered) and demodulated.

An antenna outside the metal case of an implantable device can receive EMI without relying on magnetic flux induction, and therefore without needing a coil construction. The full electromagnetic signal may interact with such an antenna, which can therefore be linear. A noise detector according to the present invention can utilize an antenna external to the metal case of the associated implantable device. For example, one or more lead lines between the implantable medical device and the patient's heart or other body area may be used as an antenna for a noise detector. Such leads are shown as 22 and 24 in FIG. 1, and as 158 in FIG. 5. To use a heart lead line as an antenna for a noise detector, for example, the lead line is connected to the receiver circuit 132 of FIG. 5, for example, through a filter to select out EMI from heart stimulus signals in the case of a stimulus lead line, or from heart sense signals in the case of a sensing lead, for example. To avoid the necessity of distinguishing EMI from the stimulus or sense signals, a separate, dedicated external antenna may be utilized for the noise detector.

Figure 9:
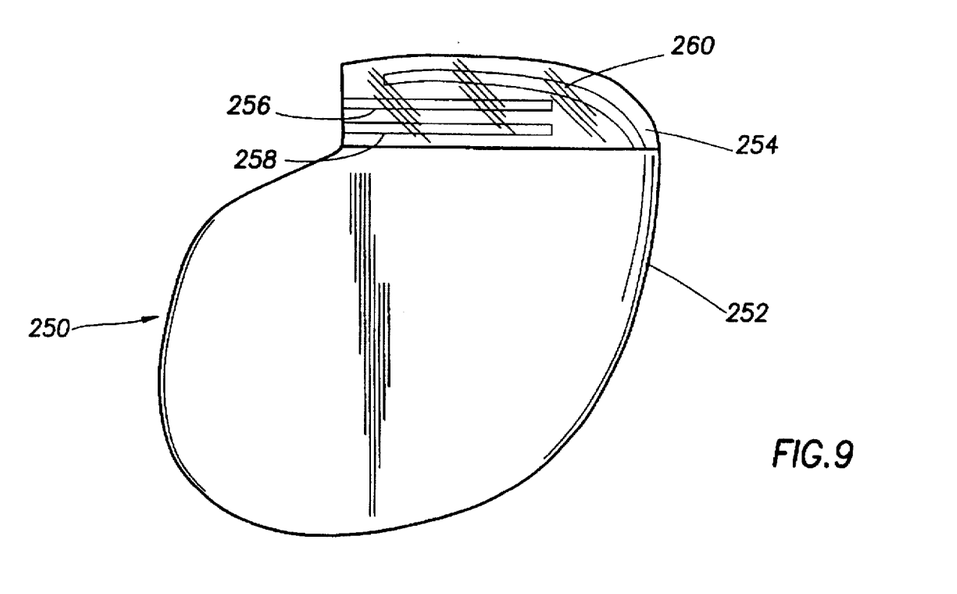
FIG. 9 is a side elevation of an implantable medical device, illustrating another type of independent, dedicated antenna which may be utilized by a noise detector according to the present invention.

FIG. 9 shows an implantable medical device 250, having a metal case 252 to house the circuitry of the device, including circuitry of a noise detector according to the present invention, and a plastic header 254. The header 254 features two elongate bores 256 and 258 that receive the leads to and from the heart, for example. Connectors (not shown) are provided adjacent the bores 256 and 258 such that insertion and sealing of a lead in either of the bores causes electrical contact between the lead and the appropriate circuit within the case 252. The stimulus and sensing leads (not shown) of a cardiac stimulator, for example, are thus connected to the circuitry of the device.

The header 254 has imbedded in it a conductive member as an antenna 260 which emerges from within the case 252 and extends along the top of the header, above the bores 256 and 258, as viewed in FIG. 9. Within the case 252 the antenna 260 may be connected into an antenna circuit such as 132 in FIG. 5, for example, in place of the coil 134. A separate coil may be added to the antenna loop of the circuit 132 to allow the circuit to be tuned. Alternatively, the antenna 260 may take the form of an elongate coil extending through the header generally as illustrated, or a short coil positioned within the end of the header. Further, a three-dimensional coil such as the antenna system 230 of FIG. 8, or a two-dimensional version thereof, may be positioned within the header 254 in place of the elongate antenna 260, for example.

From the disclosure herein it will be understood that the antenna utilized with a noise detector according to the present invention may take a variety of forms, including one or more conductive coils, or a generally linear conductive member, for example, and be located either within or outside of the metal case of the implantable medical device with which the noise detector is utilized. The antenna used by the noise detector may be shared with telemetry of the medical device, may be a lead of the medical device, or may be dedicated to use by the noise detector. Further, the noise detector may utilize a combination of such types of antennas to receive EMI. Additionally, the present invention provides a noise detector that is independent of other circuitry of the implantable medical device. In particular, the noise detector detects and processes EMI independently of the circuitry used by the implantable device to detect and process sensed signals from the patient, either physiological or nonphysiological.

The foregoing disclosure and description of the invention is illustrative and explanatory thereof, and various changes in the method steps as well as the details of the apparatus may be made within the scope of the appended claims without departing from the spirit of the invention.

What is claimed is:

1. An electromagnetic interference detector for use in a medical device that is implantable within a patient, comprising:

a. a receiver whereby electromagnetic interference signals are received;

b. an antenna as part of the receiver and on which the interference signals are received;

c. a signal detector that detects the presence of the received interference signals, the detector being independent of any other circuitry of the implantable medical device; and d. signal processing circuitry that comprises a threshold detector that selects those portions of the detected interference signals that are above a designated threshold value of a signal feature and provides a signal that depends on the presence of electromagnetic interference above the threshold value.

2. An interference detector as defined in claim 1 wherein the antenna is dedicated to the reception of electromagnetic interference.

3. An interference detector as defined in claim 1 wherein the medical device includes a telemetry circuit that communicates by utilizing the antenna.

4. An interference detector as defined in claim 3 wherein the antenna comprises a coil.

5. An interference detector as defined in claim 1 wherein the medical device includes a metal case housing circuitry of the interference detector, and the antenna comprises a conductive member extending outside the metal case.

6. An interference detector as defined in claim 1 wherein the antenna comprises a coil.

7. An interference detector as defined in claim 1 wherein the medical device has at least one electrical lead, and the antenna comprises one such electrical lead.

8. An interference detector as defined in claim 1 wherein the signal processing circuitry comprises circuitry that compares detected interference with a signal received by the medical device, including:

a. a second threshold detector that selects those portions of the signal received by the medical device that are above the designated threshold value of the signal feature; and     b. a coincidence detector that compares the portions of the interference and the signal received by the medical device that are above the designated threshold value, and provides a communication to the medical device that depends on the existence of a coincidence between the compared portions of the interference and the signal received by the medical device.

9. An interference detector as defined in claim 8 further comprising amplifiers that amplify the interference and the signal received by the medical device.

10. An interference detector as defined in claim 9 wherein the signal processing circuitry farther comprises a counter circuit which determines the time rate at which coincidences occur between the compared portions of the interference and the signal received by the medical device, and provides a communication to the medical device that depends on the occurrence of such coincidences at a time rate at least as large as a designated time rate.

11. An interference detector as defined in claim 8 further comprising first and second sampling circuits that sample the interference and the signal received by the medical device, respectively, and a timing circuit that directs the sampling by the two sampling circuits to occur at the same rate and in unison.

12. An interference detector as defined in claim 1 wherein the signal processing circuitry comprises an analog-to-digital converter which converts the detected interference signals to digital form and provides signals to the medical device indicating the strength of interference detected.

13. An interference detector as defined in claim 1 wherein the antenna comprises multiple turns of at least one coil, with the turns oriented in at least two different directions.

14. An interference detector as defined in claim 1 wherein the signal processing circuitry comprises an amplifier which amplifies the interference signals received by the antenna.

15. An interference detector as defined in claim 1 wherein the medical device comprises a cardiac stimulator.

16. An interference detector as defined in claim 1 wherein the receiver comprises a plurality of receivers, each receiver having an antenna and the antennas of the receivers are coils oriented in different directions.

17. A method of detecting electromagnetic interference in a medical device that is implantable in a patient, comprising the following steps:

a. providing a receiver circuit, including an antenna;

b. providing an electromagnetic interference detector that is independent of any other circuitry of the medical device;

c. detecting electromagnetic interference signals received on the antenna, using the detector;

d. processing the detected interference signals, including comparing them to a designated threshold value of a signal feature; and     e. providing a communication to the medical device that depends on the presence of interference above the threshold value.

18. A method as defined in claim 17 wherein the step of providing a receiver circuit comprises providing a plurality of receiver circuits, each circuit having an antenna and the antennas of the receiver circuits are coils oriented in different directions.

19. A method as defined in claim 17 wherein the step of processing the interference signals comprises converting them to digital form, and the step of providing a communication to the medical device comprises providing a communication that indicates the strength of interference detected.

20. A method as defined in claim 19 further comprising the step of providing a recording of the strength of the interference as a function of time.

21. A method as defined in claim 19 further comprising the steps of providing a recording of at least one parameter, related to the patient, as a function of time and comparing the recording of the at least one parameter as a function of time to the recording of the strength of the interference as a function of time.

22. A method as defined in claim 19 wherein the step of providing a recording of the strength of the interference as a function of time is initiated by a designated event.

23. A method as defined in claim 19 wherein the step of providing a recording of the strength of the interference as a function of time is initiated by the patient.

24. A method as defined in claim 17 wherein the steps of processing the interference signals and of providing a communication to the medical device further comprise:

a. comparing a signal received by the medical device with the designated threshold value of the signal feature and selecting those portions of the interference and the signal received by the medical device that are above the designated threshold value; and     b. comparing those portions of the interference and the signal received by the medical device that are above the designated threshold value and providing a communication to the medical device that depends on the existence of a coincidence between the compared portions of the interference and the signal received by the medical device.

25. A method as defined in claim 24 further comprising the step of counting coincidences between the compared portions of the interference and the signal received by the medical device as a function of time to determine the time rate it which the coincidences occur and providing a communication to the medical device that depends on the occurrence of such coincidences at a time rate at least as large as a designated time rate.

26. A method as defined in claim 17 further comprising the step of amplifying the interference signals received by the antenna.

27. A method as defined in claim 17 wherein the communication to the medical device that depends on the presence of interference initiates a reversion of the medical device to a designated mode of operation.

28. method as defined in claim 17 wherein the medical device is a cardiac stimulator.

29. A method as defined in claim 28 wherein the communication to the cardiac stimulator that depends on the presence of interference initiates a reversion of the cardiac stimulator to a designated noise mode.

* * * * *

UNITED STATES PATENT AND TRADEMARK OFFICE
CERTIFICATE OF CORRECTION

PATENT NO.   : 5,697,958
DATED        : December 16, 1997
INVENTOR(S)  : Patrick J. Paul and David Prutchi It is certified that error appears in the above-indentified patent and that said Letters Patent is hereby corrected as shown below:

```
On the Title page, item [56], 12th reference under U.S. Patent
Documents, change "5,151,832" to -- 5,101,832 --.
In column 5, at line 12, change "liming" to -- timing --;
            at line 13, change "liming" to -- timing --;
            at line 31, change "liming" to -- timing --; and
            at line 50, change "m" to -- to --.
In column 12, at line 45, change "lime" to -- time --; and
             at line 55, change "lime" to -- time --.
In column 15, at line 55, change "sealing" to -- seating --.
In Claim 10, at line 2, change "farther" to -- further --.
In Claim 21, at line 1, change "19" to -- 20 --.
In Claim 22, at line 1, change "19" to -- 20 --.
In Claim 23, at line 1, change "19" to -- 20 --.
In Claim 25, at line 5, change "it" to -- at --.
```

Signed and Sealed this

Seventeenth Day of March, 1998

*Attest:*

BRUCE LEHMAN

*Attesting Officer*    *Commissioner of Patents and Trademarks*